United States Patent [19]

Ramond

[11] Patent Number: 5,048,540
[45] Date of Patent: Sep. 17, 1991

[54] CONTACT UNIT EMBEDDABLE IN AN ELECTRICALLY CONDUCTIVE CASTING FOR USE IN ELECTRICAL TREATMENT FOR THERAPEUTICAL OR BEAUTY PURPOSES

[76] Inventor: Gérard Ramond, 31380 Montastruc-la-Conseillere, Gragnague, France

[21] Appl. No.: 480,612

[22] Filed: Feb. 15, 1990

[30] Foreign Application Priority Data

Feb. 17, 1989 [FR] France .................... 89 02102

[51] Int. Cl.⁵ .............................................. A61N 1/04
[52] U.S. Cl. ...................................... 128/798; 123/802
[58] Field of Search ................ 128/783, 792, 798, 802, 128/803, 640; 606/32

[56] References Cited

U.S. PATENT DOCUMENTS

| 3,606,881 | 9/1971 | Woodson | 128/2.06 E |
|---|---|---|---|
| 4,008,721 | 2/1977 | Burton | 128/802 |
| 4,082,087 | 4/1978 | Howson | 128/640 |
| 4,237,886 | 12/1980 | Sakurada et al. | 606/32 |
| 4,243,051 | 1/1981 | Witteman | 128/798 |
| 4,248,247 | 2/1981 | Ware et al. | 128/798 |
| 4,317,457 | 2/1982 | Guillot | 128/783 |
| 4,391,278 | 7/1983 | Cahalan et al. | 128/798 X |
| 4,458,696 | 7/1984 | Larimore | 128/798 |
| 4,832,036 | 5/1989 | Cartmell et al. | 128/802 |

FOREIGN PATENT DOCUMENTS

| 1340484 | 9/1963 | European Pat. Off. | |
|---|---|---|---|
| 0002059 | 5/1979 | European Pat. Off. | |
| 0004514 | 10/1979 | European Pat. Off. | |
| 0269200 | 6/1988 | European Pat. Off. | 128/798 |
| 8500017 | 1/1985 | World Int. Prop. O. | 128/802 |

Primary Examiner—Lee S. Cohen
Attorney, Agent, or Firm—Perry Carvellas

[57] ABSTRACT

A contact unit for applying current to a person's skin through an electrically conductive casting composition spread over an area of skin to be treated for therapeutical or beauty purposes. The contact unit electrically interconnects an electric current generator lead and the casting composition and comprises a flexible conductive plate made of an elastomer containing a conductive powder and in contact with the conductive core of the lead. An insulating liner overlies a first face of the plate and extends along the edge thereof and terminates flush with the second or uncovered face of the plate. The insulating liner bears against a first layer of the casting composition in contact with the person's skin. A second layer of the casting composition overlies the first layer and the second or uncovered face of the plate. Thus the electric current from the contact unit cannot flow directly through the first layer to the subjacent skin area so as to avoid burning the skin.

4 Claims, 1 Drawing Sheet

CONTACT UNIT EMBEDDABLE IN AN ELECTRICALLY CONDUCTIVE CASTING FOR USE IN ELECTRICAL TREATMENT FOR THERAPEUTICAL OR BEAUTY PURPOSES

BACKGROUND OF THE INVENTION

The invention relates to a contact unit adapted to be embedded in a mass of electrically conductive sheet or casting on one's skin for applying electric current for therapeutic or beauty purposes, the current being supplied by a suitable voltage generator, and the contact unit ensuring the electrical connection between the generator lead and the electrically conductive casting composition.

U.S. Pat. No. 4,317,457 discloses a cutaneous electrode or electrically conductive casting for treating a person's skin. The casting is prepared from a plastic binder with an electrically conductive additive. When excess water is added to the binder which is typically a dental quality plaster, a settable material is formed. The additive is a salt dissolved in the water, typically calcium chloride. In the foregoing U.S. patent at least one metal contact is embedded in the casting composition.

The electrical resistivity of the electrically conductive casting composition is substantially greater than that of a metal. A surface resistivity similar to that of one's skin must be sought in order that the skin be subjected to comparable current densities over the entire surface of the electrically conductive casting composition which means that the voltage drops between the point where current is applied to the casting and any other point along the surface of the casting is substantially the same in the casting and in the subjacent cutaneous tissue.

It has been found that beneath the zones where the metal contacts are incorporated in the casting, the current densities were greater than the average current densities along the casting. Indeed, owing to the relatively low resistivities, the metal contacts are substantially equipotential and the lines of current flow entering the casting composition are normal to the contact surface. The distance between the contact and the skin inside the casting is reduced so that the current is concentrated. This limits the effective current for treatment and increases the risk of burning the skin if the thickness of the casting is insufficient beneath the metal contact. The positioning of the embedded metal contact in the casting requires care and training and even then, the current density must be adjusted with caution.

OBJECT AND SUMMARY OF THE INVENTION

An object of the invention is to mitigate or even overcome these drawbacks.

According to the invention there is provided a contact unit adapted to be embedded in an electrically conductive casting composition applied on a person's skin for applying electric current thereto for therapeutic or beauty purposes, said contact unit being adapted to electrically interconnect a current generator lead and the electrically conductive composition, said contact unit comprising a flexible plate of conductive material having substantially parallel first and second faces and a peripheral edge therebetween, an insulating liner covering the first face of the plate and extending along the peripheral edge and terminating flush with the second, or uncovered, face, a bared end of the lead being inserted into the plate and at least a portion of the lead adapted to extend through the casting composition being sheathed with insulation.

This arrangement enables the current to be introduced into the casting along the other or uncovered face of the plate, as the liner opposes the flow of current from the first face and the peripheral edge. Thus, to some extent it is possible to select the current flow lines into the electrically conductive casting composition thereby avoiding a concentration of the current flow into a small area of skin.

Secondarily, the flat plate configuration of the contact unit is highly suitable for embedding in the casting and minimizing the risk of its displacement at the start of setting.

Preferably, the lead insulation terminates in the liner with which it fuses to minimize the risk of stray currents from the conductive core of the lead into the electrically conductive casting and the risk of the lead being pulled out of the unit.

The contact plate is preferably made of an elastomer having a conductive powder charge so as to combine the advantages of flexibility of the plate with good conductivity.

In the preferred arrangement the contact unit is embedded in an electrically conductive casting composition comprising a water settable powder and a mineral salt in ionised solution in the water with which the powder is combined, the liner of the contact unit bearing on a first layer of the casting composition which is adapted to be in contact with one's skin and second layer of the casting composition in electrical continuity with the first layer overlying the second or uncovered face of the plate.

It will be understood that the structure of the contact unit is devised and constructed with a view to obtaining the above-described arrangement, the liner preventing the flow of current directly through the layer of casting composition disposed between the contact unit and one's skin.

But the contact unit is a prefabricated element which up to the moment it is embedded into the casting material, is independent thereof. The sought after results are inherent in the contact unit itself regardless of whether it is possible through user carelessness to position the second or uncovered face of the plate facing the user's skin when embedding it in the casting composition. Accordingly the invention is directed above all to a contact unit per se as well as in oriented functional association with the electrically conductive casting composition.

These and other features and advantages of the present invention will become apparent from the description which follows, given by way of reference to the accompanying drawings.

DESCRIPTION OF THE PREFERRED EMBODIMENT

Figure 1:
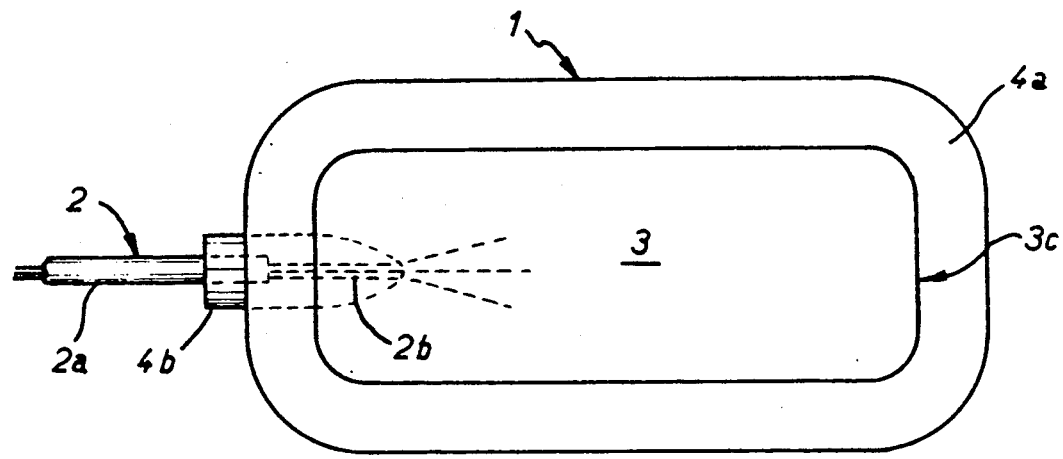
FIG. 1 is a top plan view of the contact unit embodying the present invention.
Figure 2:
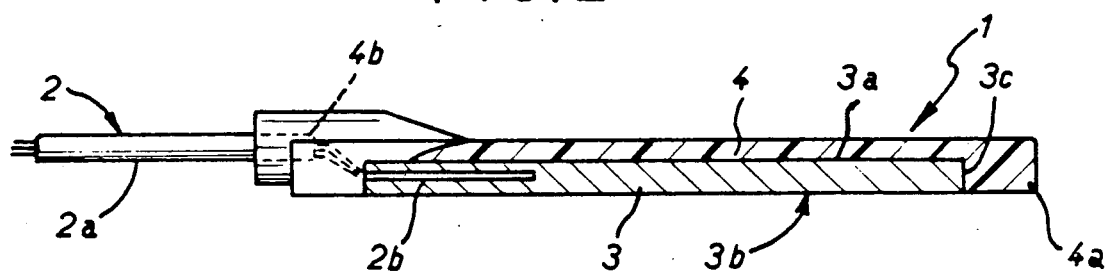
FIG. 2 is a side elevational view partially in section.

According to the illustrated embodiment of FIGS. 1 and 2 a contact unit designated generally by reference numeral 1 is adapted to electrically contact the conductive core 2b of a lead 2 and an electrically conductive sheet or casting, described below with reference to FIG. 3. comprises a plate 3 of substantially rectangular configuration and uniform thickness. The plate 3 is made of an elastomer, butyl or silicone rubber having a conductive powder charge, e.g. carbon black or metal powder, having a resistivity between 0.05 and 0.5 ohm meter.

The plate 3 has a first face 3a, a second face 3b, opposite the first face, and a peripheral edge 3c. During molding of the plate 3, the bared end of the core 2b of the lead 2 is embedded in the plate 3.

An insulating liner 4 is molded over the plate 3 and covers the first face 3a and the peripheral edge 3c. The liner 4 has a peripheral flange 4a which extends along the peripheral edge 3c of the plate 3 and terminates flush with the second face 3b of the plate 3.

The liner 4 comprises a cylindrical protruding portion 4b from the flange 4a for receiving, coaxially therewith, the end of the cable 2, the sheath or insulation 2a of the lead 2 fusing with the protruding portion 4b. The protruding portion 4b has an give-like configuration protruding from the outer surface of the liner 4.

The liner 4 may be made from polyvinyl chloride, polyamide or silicone rubber and must have a resistivity greater than $10^6$ ohm meter.

Figure 3:
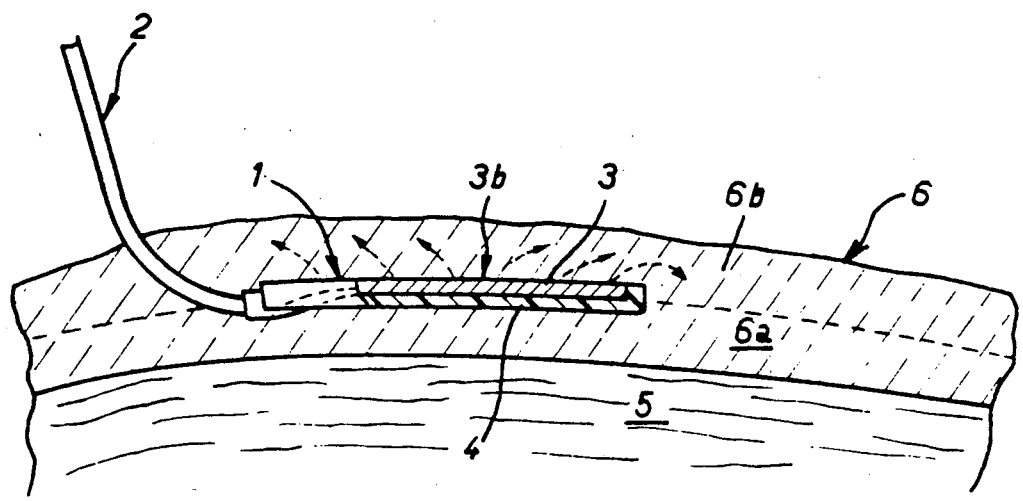
FIG. 3 is a view similar to that of FIG. 2 but on a smaller scale illustrating the embedding of the contact unit in an electrically conductive casting composition applied to a person's skin.

As illustrated in FIG. 3, in order to electrically treat a person's skin 5, a casting composition of dental quality plaster is prepared with 50 wt % water containing 4 wt % calcium chloride and 2.5 wt % glycerol and additives, in accordance with the teachings of U.S. Pat. No. 4,317,457 incorporated herein by reference.

A first layer 6a of the casting composition of uniform thickness is applied to one's skin the contact unit 1 is then positioned on the first layer 6a with its liner 4 in contact with the first layer and facing the direction of the person's skin and the second face 3b of the conductive plate facing outwardly, away from the skin 5.

As soon as thickness or consistency of the first layers starts to increase the casting 6 is completed by applying the second layer 6b which overlies the contact unit 1, in bearing contact with the second face 3b of the plate 3 and with the outer surface of the first layer 6a surrounding the contact unit so as to be in electrical continuity with the first layer. The lead 2 passes through the second layer 6b and emerges from the casting and continues to a current generator not shown).

It will be readily understood that the portion of the first layer 6a Which is located between the contact unit 1 and the person's skin 5 would otherwise provide a highly conductive pathway compared to the current flow path through the mass of the casting composition if the liner 4 did not lengthen the current flow path from the face 3b of the plate 3 to the skin 5.

It goes without saying that for sheets or castings covering large surfaces of the person's body, several contact units could be used in parallel. Moreover, the electric current generator can have two terminals each of the terminals can be connected to one or more contact units depending on the structure of the casting employed.

The invention is of course not limited to the described and illustrated embodiments, but encompasses all variations and alternatives within the scope of the appended claims.

What is claimed is:

1. A contact unit adapted to be embedded in an electrically conductive casting composition applied on a person's skin for applying electric current thereto, for therapeutic or beauty purposes, said contact unit including a lead adapted to electrically interconnect a current generator and the electrically conductive composition, said contact unit comprising a flexible plate of conductive material having a substantially parallel first face inwardly directed and a second face outwardly directed and a peripheral edge therebetween, the first face being designed to face in the direction of the person's skin and the second face being designed to face away from the person's skin, an insulating liner covering the first face of the plate and extending along the peripheral edge and terminating flush with the second, or uncovered, face, a bared end of the lead being inserted into the plate, and at least a portion of the lead adapted to extend through the casting composition being sheathed with insulation.

2. A contact unit according to claim 1, wherein the insulation sheathing the lead terminates in and is fused with the liner.

3. A contact unit according to claim 2, wherein the conductive material is an elastomer containing a conductive powder.

4. Apparatus comprising a contact unit embedded in an electrically conductive casting composition suitable for application to a person's skin for applying an appropriate electric current thereto, the casting composition comprising a powder settable when mixed with water, water containing a mineral salt ionized in solution, said contact unit comprising a flexible plate of conductive material having substantially parallel first and second faces and a peripheral edge therebetween, an insulating liner covering the first face of the plate and extending along the peripheral edge and terminating flush with the second, or uncovered, face, a lead for connecting said plate to an electric current generator, a bared end of said lead being inserted into the plate and at least a portion of the lead adapted to extend through the casting composition being sheathed with insulation, said casting composition comprising a first layer adapted to be in contact with the person's skin, said insulating liner bearing against said first layer, and a second layer in electrical continuity with said first layer and overlying said first layer and said second face of the plate.

* * * * *